United States Patent [19]

Redmond et al.

[11] Patent Number: 5,390,664
[45] Date of Patent: Feb. 21, 1995

[54] SURGICAL INSTRUMENT WITH EXTENDABLE BLADES

[75] Inventors: Russell Redmond, Goleta; Claude Vidal, Santa Barbara, both of Calif.

[73] Assignee: VIR Engineering, Santa Barbara, Calif.

[21] Appl. No.: 99,151

[22] Filed: Jul. 28, 1993

Related U.S. Application Data

[63] Continuation-in-part of Ser. No. 923,338, Jul. 31, 1992, Pat. No. 5,245,987.

[51] Int. Cl.⁶ .................................................. A61B 17/02
[52] U.S. Cl. ...................................... 128/20; 606/198
[58] Field of Search ................ 128/20, 749, 757, 759; 606/191, 198; 604/104–109, 265

[56] References Cited

U.S. PATENT DOCUMENTS 1,972,428  9/1934  Richard .
3,961,620  7/1976  Schack et al. .
5,092,345  3/1992  Sakita et al. ................... 128/757
5,152,279  10/1992  Wilk ................................ 128/17

FOREIGN PATENT DOCUMENTS 0629923  10/1978  U.S.S.R. ............................ 128/20

Primary Examiner—Max Hindenburg
Attorney, Agent, or Firm—J. E. Brunton

[57] ABSTRACT

A tissue retraction device for use in laparoscopic surgery which includes a plurality of thin, resiliently deformable, pre-stressed blades disposed in a stacked relationship within an outer sleeve. The blades are connected at their inboard ends to a support rod which is telescopically carried within the sleeve. The blades are pre-twisted about a strategically located pivot point so that once the inboard end of the device is positioned within the peritoneum, the rod can be urged forwardly causing the end portions of the blades to automatically fan out in a manner such that the full width of the blades can be pressed against the tissue.

6 Claims, 3 Drawing Sheets

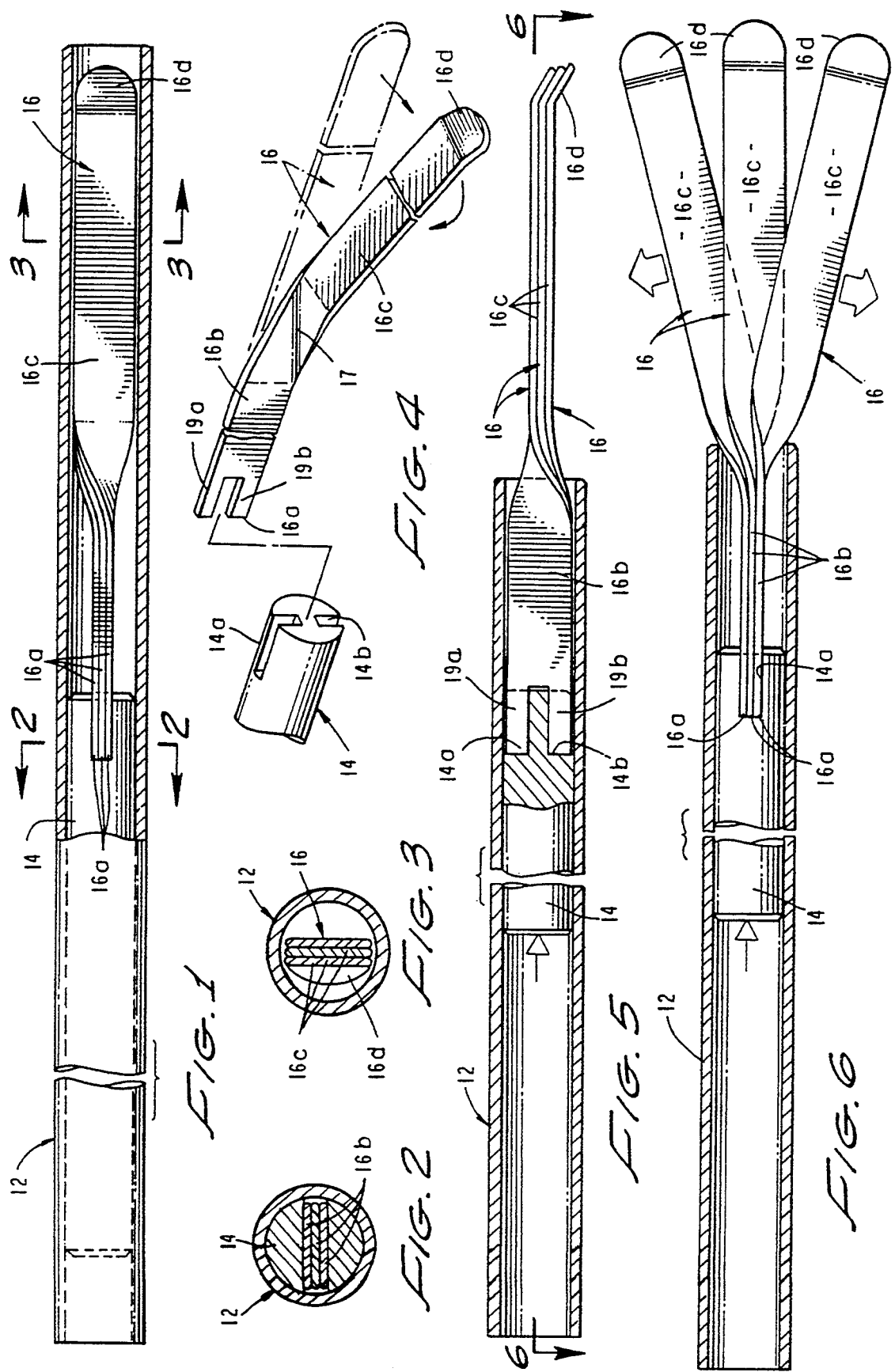

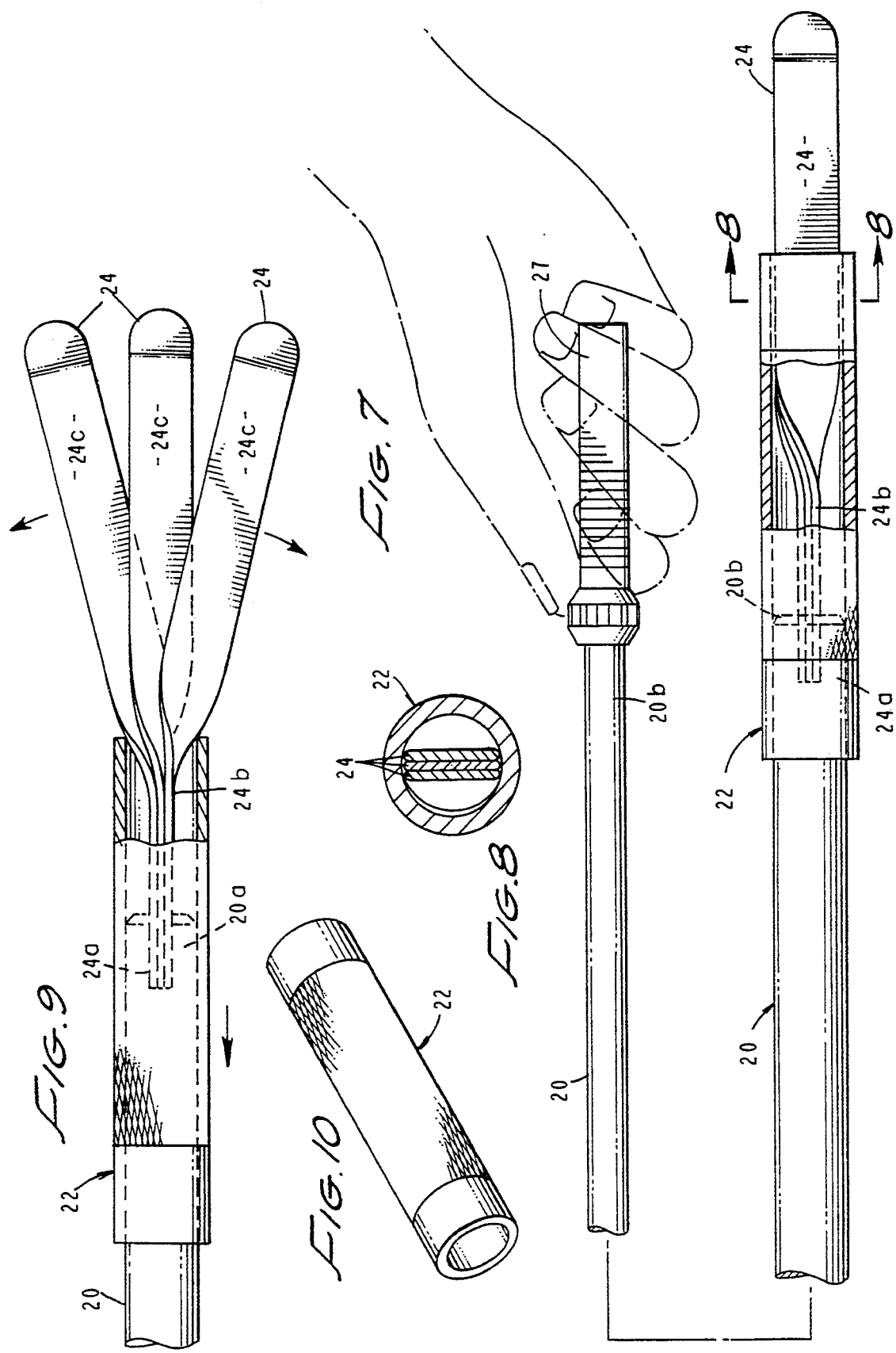

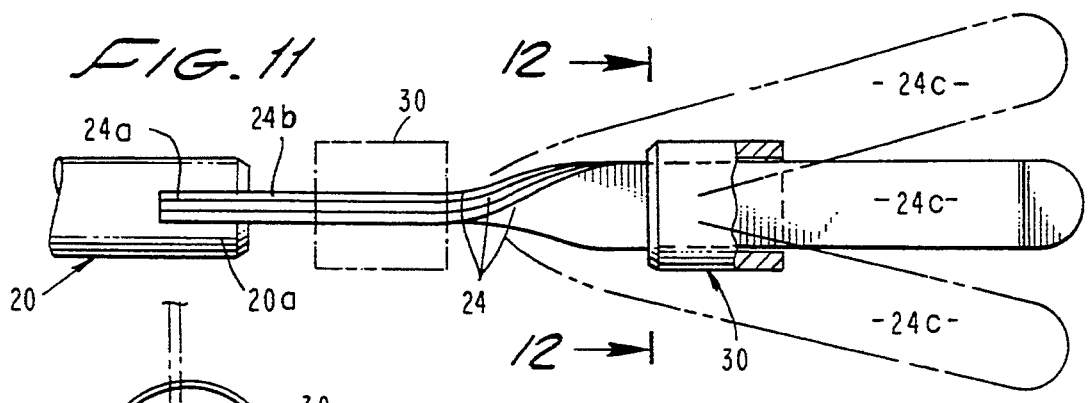
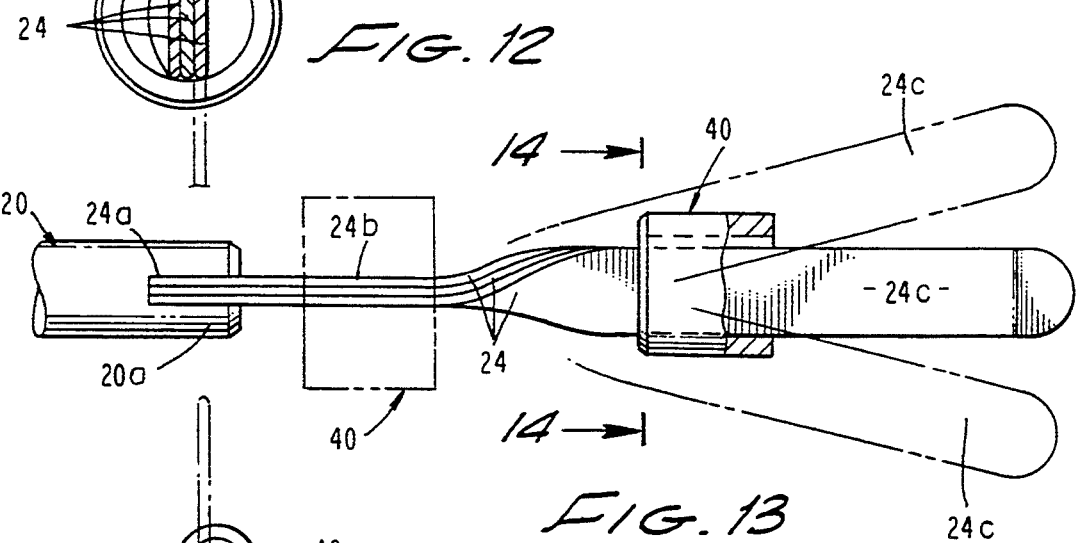
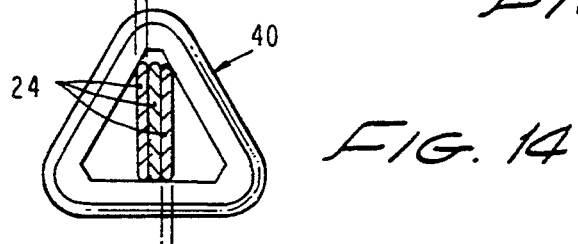
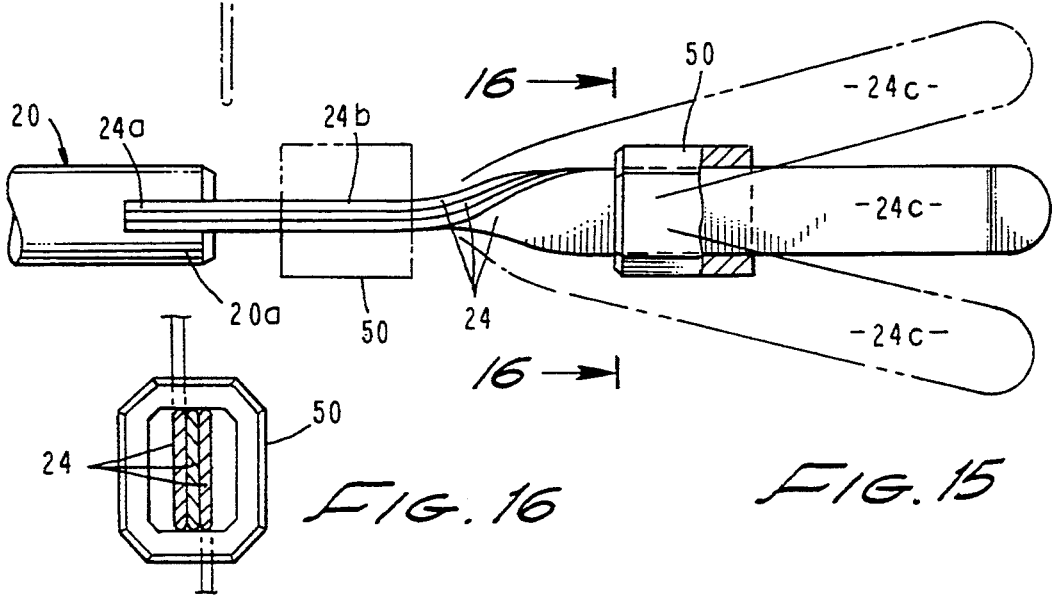
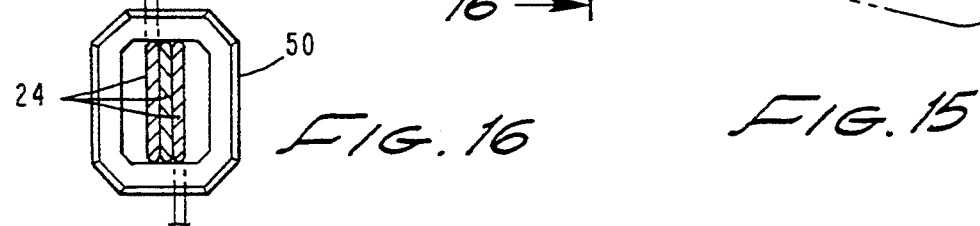

SURGICAL INSTRUMENT WITH EXTENDABLE BLADES

This is a continuation-in-part of U.S. application, Ser. No. 07/923,338, filed Jul. 31, 1992, U.S. Pat. No. 5,245,987.

BACKGROUND OF THE INVENTION

1. Field of the Invention

The present invention relates generally to surgical instruments. More particularly, the invention concerns tissue retraction device that will fit within a small diameter trocar and will open or "fan out" once within the peritoneum.

2. Discussion of the Invention

During the performance of laparoscopic surgery, the surgeon will have occasion to retract tissue and other structures from the abdominal cavity. In the past, this has typically been accomplished using graspers and retractors of various sizes and designs. As a general rule, these prior art devices are relatively large and cumbersome to work with and, on occasion, can cause serious injury to the patient.

The apparatus of the present invention, provides for the first time, a very small, easy to use instrument which will conveniently fit within a trocar as small as five millimeters in diameter. The device can include one or more specially configured blades which can be extended outwardly once the blade is in position within the peritoneum.

In one form of the invention, a plurality of thin, resiliently deformable, pre-stressed blades are provided in a stacked relationship within an outer sleeve and are connected at their inboard ends to a support rod telescopically carried within the sleeve. The blades are pre-twisted about a strategically located pivot point so that once the inboard end of the device is positioned within the peritoneum, the rod can be urged forwardly causing the end portions of the blades to automatically fan out in a manner such that the full width of the blades can be pressed against the tissue. By retracting the rod, the blades can be pulled into the sleeve and returned to their stacked and aligned configuration within the outer sleeve.

SUMMARY OF THE INVENTION

It is an object of the present invention to provide a surgical instrument which is very small but sturdy and easy to use for the retraction of tissue and the like during laparoscopic surgery.

More particularly, it is an object of the invention to provide a device of the aforementioned character which will conveniently fit within a five millimeter trocar.

Another object of the invention is to provide an instrument as described in the preceding paragraph which includes a plurality of very thin tissue engaging blades, which are stacked together during insertion of the instrument into, for example, the peritoneum, but can be caused to automatically fan out within the peritoneum so that the full width of the blades can be used for tissue manipulation.

Another object of the invention is to provide an instrument of the character described in which one or several blades can be used and in which the blades can be specially configured and formed from a wide variety of materials so that the device can be precisely tailored for a number of end uses.

Still another object of the invention is to provide an instrument as described in the preceding paragraphs which embodies a minimum number of moving parts, is easy for the surgeon to use and can be inexpensively manufactured.

BRIEF DESCRIPTION OF THE DRAWINGS

FIG. 1 is a foreshortened, top plan view, partly in cross-section to show internal construction, of one form of the surgical instrument of the present invention.

FIG. 2 is a cross-sectional view taken along lines 2—2 of FIG. 1.

FIG. 3 is a cross-sectional view taken along lines 3—3 of FIG. 1.

FIG. 4 is a generally perspective, fragmentary, exploded view of the elongated rod portion and one blade of the apparatus.

FIG. 5 is a foreshortened, side-elevational view of the apparatus partly in cross-section to show internal construction.

FIG. 6 is a view taken along lines 6—6 of FIG. 5.

FIG. 7 is a diagrammatic view, partly in cross-section, illustrating the relationship among the various components of an alternate form of the surgical instrument of the invention.

FIG. 8 is a cross-sectional view taken along lines 8—8 of FIG. 7.

FIG. 9 is an enlarged top plan view, partly in cross-section of the forward portion of the instrument showing the blades of the device in a fanned-out configuration.

FIG. 10 is an enlarged, generally perspective view of the slidable sleeve portion of the device which function to maintain the blades in a stacked configuration.

FIG. 11 is an enlarged fragmentary, top plan view of the forward portion of still another form of the surgical instrument of the invention.

FIG. 12 is a cross-sectional view taken along lines 12—12 of FIG. 11.

FIG. 13 is an enlarged fragmentary top plan view of the forward portion of yet another embodiment of the invention.

FIG. 14 is a cross-sectional view taken along lines 14—14 of FIG. 13.

FIG. 15 is an enlarged fragmentary top plan view of still another form of the invention.

FIG. 16 is a cross-sectional view taken along lines 16—16 of FIG. 15.

DESCRIPTION OF ONE FORM OF THE INVENTION

Referring to the drawings and particularly to FIGS. 1, 4, and 5, the surgical instrument of the present invention can be seen to comprise an elongated, generally cylindrically-shaped sleeve 12 and an elongated, cylindrically-shaped rod 14 which can be telescopically received within sleeve 12 for sliding movement from the retracted position shown in FIG. 1 to the extended position shown in FIG. 6. As best seen in FIG. 6, the apparatus of this form of the invention also includes a plurality of thin, yieldably deformable blades 16 which are connected to rod 14 proximate their inboard ends 16a.

Referring also to FIGS. 2 and 3, it is to be noted that when the rod 14 is in the retracted position, blades 16 reside within the sleeve in a stacked relationship with the planar surfaces of the blades being in close proximity with one another. It is also to be noted that each of the blades 16 has a longitudinal axis which is coaxially aligned with the longitudinal axis of sleeve 14.

As illustrated in FIG. 4, each of the blades 16 is twisted out of plane along a diagonally extending line 17, which is located at the junction of first and second portions 16b and 16c of the blade. Each of the blades is constructed of a resiliently deformable material such as spring steel or plastic so that, after portion 16c is twisted relative to portion 16b, it will tend to return to its original non-twisted configuration. Stated another way, when the blades are twisted about the longitudinal axis of the blades and along junction line 17, internal stresses will be imparted to the blades tending to continuously urge the second portion of the blades toward their original non-twisted configuration relationship. As a result of these internal stresses, when the rod 14 is moved into its second or extended position as shown in FIG. 6, the blades will tend to automatically fan out with respect to one another in the manner shown in FIG. 6, with the second portion of each of the blades coming to rest in a plane that extends at an obtuse angle with respect to the plane of the first portion of the blade.

When rod 14 is returned to its retracted position, the blades will enter the open end of sleeve 12 and will once again be urged into the stacked and aligned relationship shown in FIG. 1. Advantageously, the twisted portions of the blades provide camming surfaces to assist in smoothly urging the blades into their stacked orientation as they are drawn back into the sleeve. More particularly, as noted in FIGS. 2 and 3, when the blades are in the stowed position within sleeve 12, the first portion 16b of each blade resides in a plane which is generally perpendicular to the plane of each of the blade portions 16c. Because the width of the blades closely correspond to the diameter of the sleeve, the blades will be held in this stacked configuration so long as they are retained within sleeve 12. However, once rod 14 is pushed forwardly, as illustrated in FIG. 6, the memory retained by the second portion of each of the blades 16 will cause the blades to attempt to return to their original non-twisted configuration and, as a result, the blades will fan out or spread apart in the finger-like manner illustrated in FIG. 6. In this position, the full width of the blades have substantial strength due to the intermediated, twisted portion of each blade and, therefore; can advantageously be pressed against the tissue.

Referring once again to FIG. 4, it is to be noted that support 14 is provided with a pair of diametrically opposed slots 14a and 14b. Similarly, each of the blades 16 is provided with a pair of spaced-apart ears 19a and 19b which are closely receivable within slots 14a and 14b of rod 14. With this construction, each of the blades is securely anchored at its inboard end to rod 14 so that portion 16b of each blade is restrained against movement about its longitudinal axis. However, such anchoring of the blades does not impede the tendency of the second portions 16c of the blades to out of the plane and into the configuration shown in FIG. 6.

In the form of the invention shown in the drawings, each of the blades is provided with an outboard tip portion 16d which is disposed in a plane that extends at an angle with respect to the plane of portion 16c of the blade. Tip portions 16d are useful in the manipulation of tissue during the surgical procedure.

While blades 16 can be constructed of various materials and have various sizes, the instrument of the present invention is ideally suited for use in connection with a laparoscopic surgery. Therefore, the blades 16 are very small and preferably are of a size that can be received within a 5 millimeter trocar. For certain end applications, blades 16 can be coated with a lubricating material, or a protective coating, or they can otherwise be specially treated. By way of example, each blade could be provided with a Dacron, reinforced silicon sheeting which is vulcanized around the blade. Such blades would provide a soft, non-sticking surface which would facilitate the manipulation of tissue during the surgical procedure.

As appropriate, the sleeve, the blades and the elongated rod 12, can be constructed of metal, plastic or other suitable material. When the components are constructed of a plastic material, the apparatus can be manufactured so inexpensively that disposal of the instrument after each use is economically warranted.

Turning now to FIGS. 7 through 9, an alternate form of the surgical instrument of the invention is there illustrated. This form of the invention, which is usable in open surgery procedures, comprises an elongated, generally cylindrically-shaped rod 20 which can be telescopically received within a much shorter sleeve 22. Sleeve 22, which comprises the blade constraining means of the invention, is slidably movable relative to rod 20 from the forward, extended position shown in FIG. 7 to the retracted position shown in FIG. 9. As before, the apparatus of this form of the invention includes a plurality of thin, yieldably deformable blades 24 which are connected to rod 20 proximate their inboard ends 24a.

Referring particularly to FIG. 7, when sleeve 22 is in the forward, extended position, blades 24 are constrained within the sleeve in a stacked relationship with the planar surfaces of the blades being in close proximity with one another. Blades 24 are of similar construction to the previously described blades 16, with each having a longitudinal axis that is coaxially aligned with the longitudinal axis of sleeve 22. Additionally, as before, each of the blades is twisted out of plane along a diagonally extending line, which is located at the junction of first and second portions 24b and 24c of the blade. Once again the blades are constructed of a resiliently deformable material such as spring steel or plastic so that, after portion 24c is twisted relative to portion 24b, it will tend to return to its original non-twisted configuration.

As a result of these internal stresses formed within the blades, when sleeve 22 is moved into its second or retracted position as shown in FIG. 9, the blades will tend to automatically fan out with respect to one another in the manner shown. However, when sleeve 22 is returned to its forward position as shown in FIG. 7, the blades will enter the open end of the sleeve and will once again be urged into the stacked and aligned relationship shown and in the configuration previously described in connection with the first embodiment of the invention.

Because the width of the blades closely corresponds to the diameter of the sleeve, the blades will be held in the stacked configuration shown in FIG. 7 so long as they are retained within sleeve 22. However, once the sleeve is retracted, as illustrated in FIG. 9, the memory retained by the second portion of each of the blades will cause the blades to attempt to return to their original non-twisted configuration, and, as a result, the blades will fan out or spread apart in the finger-like manner illustrated in FIG. 9 with the longitudinal axis of the second portion of the blades extending angularly with respect of one another.

As was the case in the earlier described embodiment, each of the blades is securely anchored at its inboard end to the first end 20a of rod 20 in the manner previously described so that portion 24b of each blade is restrained against movement about its longitudinal axis. Due to the novel configuration of the blades, the tip portions thereof are useful in the manipulation of tissue during the surgical procedure and the instrument is ideally suited for use in connection with various types of open surgery procedures. As before, for certain end applications, the blades can be coated with a lubricating material, or a protective coating, or they can otherwise be specially treated. The sleeve and the elongated rod 20 can be constructed of metal, plastic or other suitable material. Provided proximate the second end 20b of rod 20, is a handle 27 which includes an enlarged diameter forward portion 29 for assisting the surgeon in gripping and manipulating the device.

Referring next to FIGS. 11 and 12, still another embodiment of the surgical instrument of the present invention is there shown. This embodiment is similar in many respects to the previously discussed embodiments and like numbers have been used in the drawings to designate like components. For example, rod 20 as well as blades 24 are of identical construction to that previously described and the blades are interconnected with rod 20 in the manner previously discussed. However, the blade constraining means, or sleeve portion 30, of this form of the invention is of slightly different configuration being substantially shorter in length than previously identified sleeve 22. More specifically, sleeve 30 is uniquely configured so as to have a diameter substantially equal to its length.

As indicated in FIG. 12, sleeve 30 is generally circular in cross-section at any point as was previously identified sleeve 22. The inner diameter of ring shaped sleeve 30 closely corresponds to the width of blades 24 when the blades are in the stacked configuration shown in FIG. 12. With this construction, when the ring-like sleeve 30 is in the retracted position shown by the dotted lines in FIG. 11, it closely surrounds portions 24b of the blades 24. However, when ring-shaped member 30 is in its forward or extended position shown by the solid lines in FIG. 11, it encapsulates portions 24c of the blades so they reside in a stacked relationship with the planar surfaces thereof being in close proximity with one another.

As before, each of the blades is constructed of a resiliently deformable material such as spring steel so that, after portion 20c of each blade is twisted relative to portion 20b, it will tend to return to its original non-twisted configuration. When ring-shaped sleeve 30 is in the extended position shown in the solid lines of FIG. 11, it restrains the blades from moving into their fanned out position. However, when the ring-shaped member 30 is moved relative to the blades into the position indicated by the dotted lines in FIG. 7, the blades will tend to automatically fan out with respect to one another in the manner shown by the phantom lines in FIG. 12. The orientation of the blades in this fanned out configuration is identical to that previously described herein.

A study of FIGS. 11 and 12 reveals that, while sleeve 30 is telescopically receivable over the first end 20a of rod 20, it need not be moved over rod 20 in order to function in a manner to restrain blades portion 24c in their stacked configuration. Rather, so long as sleeve 30 can be moved relative to blades 24 from the position shown in the solid lines in FIG. 12 to the position shown in the dotted lines in FIG. 12, it will function to either maintain the blades in a stacked aligned relationship or conversely to permit them to fan out into the orientation shown by the phantom lines in FIG. 11.

Turning to FIGS. 13 and 14, yet another embodiment of the surgical instrument of the present invention is there shown. Once again this embodiment is similar in most respects to the embodiment just described and like numbers are used to identify like components. However, in this latest embodiment of the invention, the blade constraining means comprises a member 40 which is generally triangular in cross section. Member 40 has an internal opening substantially corresponding in size to the width of blades 24 and, as shown in FIG. 14, constrains blades 24 in a stacked relationship when the member is in the forward or extended position shown by the solid lines in FIG. 40.

Member 40 is slidably movable relative to blades 24 from the position shown in the solid lines in FIG. 13 to the position shown in the phantom lines in FIG. 13 wherein it encapsulates portions 24b of blades 24. As indicated in FIG. 13, when the constraining means or member 40 is in the retracted position, portions 24c of blades 24 are free to fan out in the configuration shown in FIG. 13 and in the manner described in detail in connection with the previously described embodiments of the invention.

Turning now to FIGS. 15 and 16, still another form of the surgical instrument of the present invention is there described. Once again, like numerals have been used to describe like components to those previously described herein. This latest form of the invention is virtually identical to the previously described embodiment and operates in substantially the same way. However, the constraining means in this last form of the invention, comprises a rigid member 50 which is generally rectangular in shape and is provided with an internal opening substantially corresponding to the width of the blades 24. Once again, when member 50 is in the forward or extended position, it constrains blades 24 into the stacked relationship previously described. However, when member 50 is moved to the retracted position shown by the phantom lines in FIG. 15, the blades are once again free to fan out into the configuration shown in FIG. 15 and as previously described herein.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A surgical instrument for use in connection with the performance of laparoscopic procedures, comprising:
   (a) an elongated, generally cylindrically shaped rod having first and second ends, said second end having a handle portion;
   (b) first and second yieldably deformable, generally planar blades connected to said rod proximate said first end and extending therefrom, each of said blades having curved tip portions and spaced apart, generally parallel edges, each said blade having a width, a longitudinal axis and a first and second portion, said first portions being disposed in first planes and said second portions being twisted about said longitudinal axis at a location proximate the junction of said first and second portions to urge said second portions into second planes generally perpendicular to said first planes, whereby internal stresses are imparted to said blades tending to cause said second portions of said blades to fan outwardly with respect to one another so that said edges of said second portion of said first blade extend angularly with respect to said edges of said second portion of said second blade and said tip portions of said second portions of said first and second blades are angularly spaced apart; and (c) blade constraining means for constraining movement of said blade, said means being telescopically receivable over said blades for sliding movement with respect thereto from an extended position to a retracted position, said means in said extended position functioning to restrain said blades from fanning out with respect to each other.

2. An instrument as defined in claim 1 in which said blade constraining means comprises a member having an internal opening substantially corresponding in size to said width of said blades.

3. An instrument as defined in claim 2 in which said member comprises a sleeve which is generally circular in cross section.

4. An instrument as defined in claim 2 in which said member is generally rectangular in cross section.

5. An instrument as defined in claim 2 in which said member is generally triangular in cross section.

6. An instrument as defined in claim 2 in which said member has a length substantially equal to said internal opening.

* * * * *